(12) United States Patent
Salamone et al.

(10) Patent No.: US 8,426,143 B2
(45) Date of Patent: Apr. 23, 2013

(54) GEMCITABINE IMMUNOASSAY

(75) Inventors: Salvatore J. Salamone, Stockton, NJ (US); Jodi Blake Courtney, Doylestown, PA (US); Howard Sard, Arlington, MA (US); Christopher Spedaliere, Allentown, PA (US)

(73) Assignee: Saladax Biomedical Inc., Bethlehem, PA (US)

( * ) Notice: Subject to any disclaimer, the term of this patent is extended or adjusted under 35 U.S.C. 154(b) by 26 days.

(21) Appl. No.: 13/114,218

(22) Filed: May 24, 2011

(65) Prior Publication Data

US 2012/0301901 A1 Nov. 29, 2012

(51) Int. Cl.
*G01N 33/53* (2006.01)
(52) U.S. Cl.
USPC .............................. 435/7.1; 435/7.93; 436/56
(58) Field of Classification Search .................. None
See application file for complete search history.

(56) References Cited

U.S. PATENT DOCUMENTS

| 7,569,358 | B2 | 8/2009 | Salamone et al. | |
|---|---|---|---|---|
| 7,803,785 | B2 | 9/2010 | Gallop et al. | |
| 7,829,064 | B2 | 11/2010 | Griffiths et al. | |
| 2005/0130270 | A1* | 6/2005 | Cupo et al. | 435/70.21 |
| 2010/0068827 | A1 | 3/2010 | Salamone et al. | |
| 2010/0204456 | A1 | 8/2010 | Salamone et al. | |
| 2011/0086111 | A1 | 4/2011 | Lee et al. | |

OTHER PUBLICATIONS

The International Search Report and Written Opinion by the International Searching Authority, issued on Jul. 30, 2012, in the related PCT application No. PCT/US12/36723.

\* cited by examiner

*Primary Examiner* — Shafiqul Haq

(57) ABSTRACT

The present invention comprises novel analogs of gemcitabine and novel gemcitabine immunogens leased out of, i.e., derived from, the 5'-hydroxy position of gemcitabine. The invention also comprises unique monoclonal antibodies generated using gemcitabine linked immunogens as well as unique conjugates and tracers which antibodies, conjugates, and tracers are useful in immunoassays for the quantification and monitoring of gemcitabine in biological fluids.

10 Claims, No Drawings

GEMCITABINE IMMUNOASSAY

FIELD OF THE INVENTION

This invention relates to the field of immunoassays for determining the presence or quantifying the amount of gemcitabine in human biological samples in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other to tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Gemcitabine is a commonly used cytotoxic agent that is used for the treatment of Pancreatic Cancer; Poplin et al *J Clin Oncol*, 27, 23, 3778-85, 2009 and Non-Small Cell Lung Cancer; Zinner, R G, et al., Int J Radiat Oncol Biol Phys, 73, 1, 119-27 2009; and Treat, J A, et al., Ann Oncol, 2009. Gemcitabine is also used as an adjuvant treatment in pancreatic cancer (Saif, M W, JOP, 10, 4, 373-7 2009; Li, J and M W Saif, JOP, 10, 4, 361-5 2009). Although it is widely used, this compound has been associated with debilitating side effects such as myelosupression, along with liver and kidney damage. By monitoring the levels of gemcitabine in the body and adjusting the dose these side effects can be better controlled and limited in patients.

Gemcitabine is the hydrochloride salt of the formula:

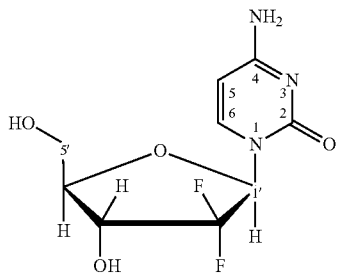

I

There is often high variable relationship between the dose of gemcitabine and the resulting serum drug concentration that affects therapeutic effect. This is especially prevalent in women and elderly patients. These groups display a lower clearance, resulting in higher plasma concentrations for any given dose. Gemcitabine (I) is metabolized in the body by cytidine deaminase (CDA) to its main pharmaceutically inactive metabolite: 2',2'-difluoro-2'-deoxyuridine (dFdU) which has the formula:

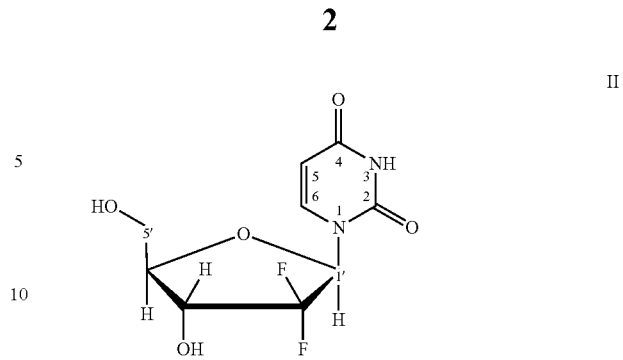

II

In preparing human biological samples such as blood and plasma samples for immunoassays it is necessary to use tetrahydrouridine (THU). This preservative acts to inhibit cytidine deaminase activity during the collection of patient samples to prevent further metabolism of gemcitabine to the inactive metabolite of the compound of formula II. The preservative tetrahydrouridine has the following formula:

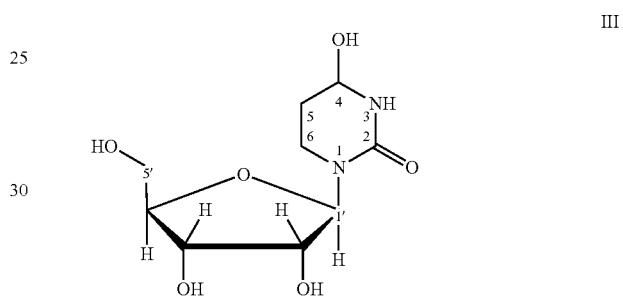

III

The degree of intra- and inter-individual pharmacokinetic variability of gemcitabine varies greatly and is impacted by many factors, including:
  Organ function
  Genetic regulation
  Disease state
  Age
  Time of sampling,
  Mode of drug administration, and
  Technique-related administration.

As a result of this variability, equal doses of the same drug in different individuals can result in dramatically different clinical outcomes, as illustrated below (Hon, Y Y and W E Evans, Clin Chem, 44, 2, 388-400 1998.). The effectiveness of the same gemcitabine dosage varies significantly based upon individual drug metabolism and the ultimate serum drug concentration in the patient. Therapeutic drug management would provide the clinician with insight on patient variation in both oral and intravenous drug administrations. With therapeutic drug management, drug dosages could be individualized to the patient, and the chances of effectively treating the cancer without the unwanted side effects would be much higher (Nieto, Y, Curr Drug Metab, 2, 1, 53-66 2001).

In addition, therapeutic drug management of gemcitabine would serve as an excellent tool to ensure compliance in administering chemotherapy with the actual prescribed dosage and achievement of the effective serum concentration levels. It has been found that variability in serum concentration is not only due to physiological factors, but can also result from variation in administration technique (Caffo, O, S Fallani, E Marangon, S Nobili, M I Cassetta, V Murgia, F Sala, A Novelli, E Mini, M Zucchetti and E Galligioni, Cancer Chemother Pharmacol, 2010).

Routine therapeutic drug management of gemcitabine would require the availability of simple automated tests adaptable to general laboratory equipment. Tests that best fit these criteria are immunoassays such as a radioimmunoassay and an enzyme-linked immunosorbent assay. However the corresponding antibodies used in these immunoassays must demonstrate a broad cross-reactivity to gemcitabine, without any substantial activity to non-pharmaceutically active gemcitabine metabolites and the preservative of formula III. In order to be effective in monitoring drug levels of gemcitabine, the antibody should be most specific to the active compound, gemcitabine and display very low cross-reactivity to no cross-reactivity to the non-pharmaceutically active metabolite, 2',2'-difluoro-2'-deoxyuridine (the compound of Formula II) and the preservative tetrahydrouridine (the compound of Formula III).

SUMMARY OF INVENTION

In accordance with this invention, a new class of antibodies have been produced which are substantially selectively reactive to gemcitabine so as to bind to gemcitabine without any substantial cross reactivity to non-pharmaceutically active gemcitabine metabolites, particularly 2',2'-difluoro-2'-deoxyuridine. In addition these antibodies do not react with the preservative, tetrahydrouridine, which is necessary in collecting patient samples to stabilize the gemcitabine in the collected patient samples. By selectively reactive, it is meant that these antibodies only react with the pharmaceutically active gemcitabine molecule and do not substantially react with the non-pharmaceutically active gemcitabine metabolites, the most important and basic blocking metabolite being 2',2'-difluoro-2'-deoxyuridine and the preservative, tetrahydrouridine.

It has been found that by using immunogens which are conjugates of an immunogenic carrier having a reactive thiol or amino functional group with 5-substituted gemcitabine compounds of the formula:

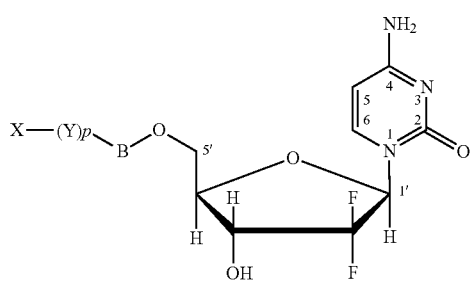

IV wherein B is —$CH_2$— or

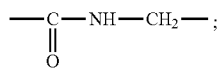

Y is an organic spacing group;
X is a functional group capable of binding to said carrier through said amino or thiol group; and
p is an integer from 0 to 1 or salts thereof; produce antibodies which are specific for gemcitabine and do not substantially react with or bind with non-pharmaceutical active metabolites particularly 2',2'-difluoro-2'-deoxyuridine as well as tetrahydrouridine. The provision of these antibodies which substantially selectively react with gemcitabine and do not cross react with 2',2'-difluoro-2'-deoxyuridine and tetrahydrouridine allows one to produce an immunoassay which can specifically detect and monitor gemcitabine in the fluid samples of patients being treated with gemcitabine. Also included within this invention are reagents and kits for said immunoassay.

DETAILED DESCRIPTION

In accordance with this invention, a new class of antibodies is provided which are substantially selectively reactive with gemcitabine and do not substantially react or cross react with pharmaceutically inactive gemcitabine metabolites, particularly 2',2'-difluoro-2'-deoxyuridine and the preservative, tetrahydrouridine. It has been discovered that through the use of these derivatives of the compound of Formula IV or salts thereof, as immunogens, this new class of antibodies of this invention are provided. It is through the use of these antibodies that an immunoassay, including reagents and kits for such immunoassay for detecting and/or quantifying gemcitabine in blood, plasma or other body fluid samples has been developed. By use of this immunoassay, the presence and amount of gemcitabine in body fluid samples, preferably a blood or plasma sample, can be detected and/or quantified. In this manner, a patient being treated with gemcitabine can be monitored during therapy and his treatment adjusted in accordance with said monitoring. By means of this invention one achieves the therapeutic drug management of gemcitabine in cancer patients being treated with gemcitabine as a chemotherapeutic agent.

The reagents utilized in the assay of this invention are conjugates of a carrier containing a reactive thiol or amino group with the compounds of Formula IV or salts thereof. Preferably the carriers contain a polyamine polymer, which contains a reactive thiol or amino group. In preparing the immunogens, the carriers are immunogenic polymers which preferably contain a polyamine polymer, having a reactive thiol or amino group. When used in an immunoassay, these conjugates are competitive binding partners with the gemcitabine present in the sample for the binding with the antibodies of this invention. Therefore, the amount of conjugate reagent which binds to the antibody will be inversely proportional to the amount of gemcitabine in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of gemcitabine in a sample is determined by correlating the measured amount of the bound or unbound conjugate produced by the gemcitabine in the sample with values of the bound or unbound conjugate determined from a standard or calibration curve obtained from samples containing known amounts of gemcitabine, which known amounts are in the range expected for the sample to be tested. These studies for producing calibration curves are determined using the same immunoassay procedure as used for the sample.

The conjugates, which include the immunogens, are prepared from compounds of the formula IV or salts thereof. The carriers, including the immunogens, having a reactive terminal amino or thiol group, are linked to the ligand portion which has the formula:

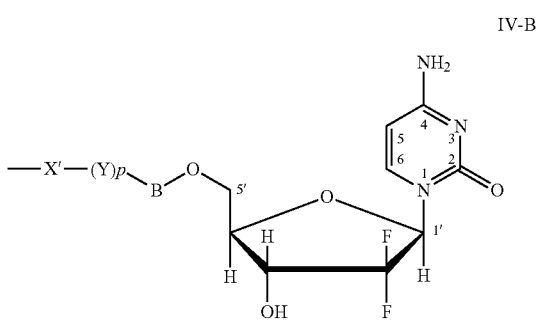

IV-B wherein X' is —CH₂— or a functional linking group, Y, B and p are as above.

This ligand portion may be linked to one or more active thiol or amino sites on the carrier containing the polyamine polymer. Preferably these carriers contain a polymer, most preferred a polyamine polymer, containing a reactive thiol or amino group.

Definitions

Throughout this description the following definitions are to be understood:

The term gemcitabine includes gemcitabine as well as the pharmaceutically acceptable salts of gemcitabine.

The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula IV and a large molecule, such as a carrier or a polyamine polymer, particularly protein. In the conjugate the small molecule maybe joined at one or more active sites on the large molecule. The term conjugate includes the term immunogen.

"Haptens" are partial or incomplete antigens. They are carrier-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is gemcitabine.

As used herein, a "spacing group" or "spacer" refers to a portion of a chemical structure which connects two or more substructures such as haptens, carriers, immunogens, labels, or tracers through a CH₂ or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein or a protein modified to carry a reactive thiol or amino group, that can join with a hapten, in this case gemcitabine, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized. Alternatively these proteins can be modified so as to contain a reactive thiol group.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide may also contain polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, Streptococcus, Staphylococcus aureus, E. coli, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the NH₂ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins. These polymer peptides can be modified by conventional means to convert the reactive NH$_2$ terminal group into a terminal SH group.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to the functional group X in the compounds of the formula IV.

The term "reagent kit," or "test kit," refers to an assembly of materials that are used in performing an assay. The reagents can be provided in packaged combination in the same or in separate containers, depending on their cross-reactivity and stabilitiy, and in liquid or in lyophilized form. The amounts and proportions of reagents provided in the kit can be selected so as to provide optimum results for a particular application. A reagent kit embodying features of the present invention comprises antibodies specific for gemcitabine. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate of gemcitabine is constructed to compete with the gemcitabine in the sample for binding sites on the antibodies. In the immunoassay of this invention, the reagents are the conjugates of the 5' substituted gemcitabine derivatives of the compounds of formula IV and the antibodies having the aforementioned requisite properties. In the compounds of formula IV-B, the linker spacer constitutes the —B—(Y)$_p$—X' portion of this molecule. In these linkers X' and the spacer —B—(Y)$_p$—X' are conventional in preparing conjugates and immunogens. Any of the conventional spacer-linking groups utilized to prepare conjugates and immunogens for immunoassays can be utilized in the compounds of formula IV-B. Such conventional linkers and spacers are disclosed in U.S. Pat. No. 5,501,987 and U.S. Pat. No. 5,101,015.

Among the preferred spacer groups are included the spacer groups hereinbefore mentioned. Particularly preferred spacing groups are groups such as alkylene containing from 1 to 10 carbon atoms,

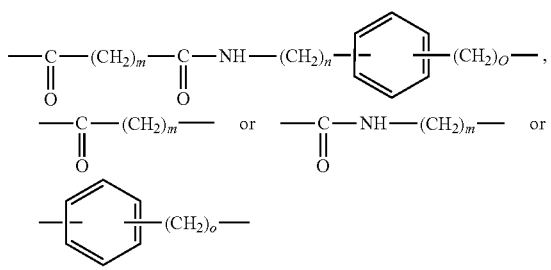

wherein n and o are integers from 0 to 6, and m is an integer from 1 to 6 with alkylene being the especially preferred spacing group. With respect to the above structures of the spacing group designated by Y, the functional group X is connected at the terminal position at the right side of the structure i.e. where (CH$_2$)m and (CH$_2$)o are located.

In the compounds of formula IV-B, X' is —CH$_2$— or a functional group linking the spacer, to an amine or thiol group on the polymeric carrier. The group X' is the result of the terminal functional group X in the compounds of Formula IV which is capable of binding to the amino or thiol group in the polyamine polymer used as either the carrier or as the immunogen. Any terminal functional group capable of reacting with an amine or thiol group can be utilized as the functional group X in the compounds of formula IV. These terminal functional groups preferably included within X are:

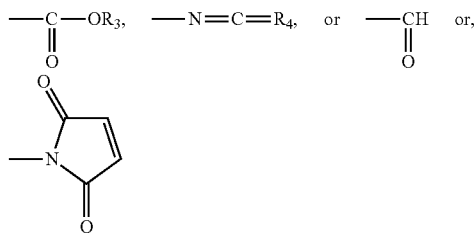

wherein R$_3$ is hydrogen or taken together with its attached oxygen atom forms a reactive ester and R$_4$ is oxygen or sulfur. The —N═C═R$_4$, radical can be an isocyanate or as isothiocyanate. The active esters formed by —OR$_3$ include imidoester, such as N-hydroxysuccinamide, 1-hydroxy benzotriazole and p-nitrophenyl ester. However any active ester which can react with an amine or thiol group can be used.

The carboxylic group and the active esters are coupled to the carrier or immunogenic polymer by conventional means. The amine group on the polyamine polymer, such as a protein, produces an amide group which connects the spacer to the polymeric immunogens or carrier to form the conjugates of this invention.

When X in the compound of formula IV is

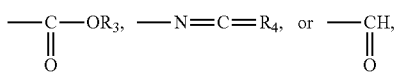

these compounds preferably react with the free amino group of the polymeric or immunogenic carrier.

On the other hand, when X in the compound of formula IV is the maleimide radical of the formula

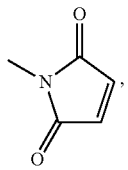

this compound preferably reacts with the thiol (or SH) group which may be present on the polymeric or protein carrier, including the immunogens. In this case where X is the maleimide radical the compound of the formula IV has the structure:

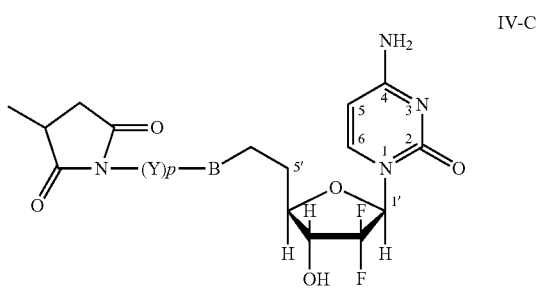

In accordance with a preferred embodiment, these compounds of formula IV-C are reacted to attach to a polymeric protein which has been modified to convert an amino group to a thiol group. This can be done by the reacting a free amino group of a polymeric protein carrier with a compound of the formula

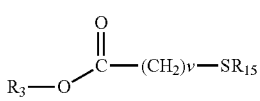

wherein $R_{15}$ is a thiol protecting group;
$R_3$ is as above; and
v is an integer of from 1 to 4.

This reaction is carried out in an aqueous medium by mixing the protein containing carrier with the compound of formula V in an aqueous medium. In this reaction temperature and pressure are not critical and the reaction can be carried out at room temperature and atmospheric pressure. Temperatures of from 10° C. to 25° C. are generally preferred. In the compound of Formula V which is reacted with the compound of Formula IV-C, any conventional thiol protecting agent can be utilized. The thiol protecting groups are well known in the art with 2-pyridyldthio being the preferred protecting group. By this reaction, the thiol group, SH— becomes the functional group of the carrier which bonds the compound of formula IV to the remainder of the carrier In the next step, before reacting with the compound of Formula IV-C with the thiol modified carrier, the thiol protecting group of carrier is removed by conventional means from the resulting reaction product which is formed by reacting the compound of formula V with the carrier. Any conventional means for removing a thiol protecting group can be utilized in carrying out this reaction. However, in utilizing a means to remove the thiol protecting group, care must be taken that the reactants be soluble in the aqueous medium and do not in any way destroy or harm the polyamine polymer contained in the carrier. A preferred means for removing this protecting group is by the use of dithiothreitol as an agent to reduce the resultant condensation product. This reduction can be carried out by simply adding the reducing agent to the reaction medium without utilizing higher pressures or temperatures. This reduction can be carried out at room temperature and atmospheric pressure.

While the above method represents one means for converting a reactive terminal amino group on the polyamine polymeric containing carrier to a thiol group, any conventional means for carrying out this conversion can be utilized. Methods for converting terminal amino groups on polyamine polymeric containing carriers to thiol groups are well known in the art and can be employed in accordance with this invention.

The reaction of the polymeric polyamine containing carrier having a terminal reactive thiol group with the compound of formula IV where X is a functional group capable of binding to the terminal thiol group carried by the carrier can be carried out by conventional means. The maleimide of IV C is reacted with the thiol group carried by the polyamine polymeric carrier. Any well known means for addition of a thiol across a maleimide double bond can be utilized in producing the conjugates of formula IV which are conjugated through a thiol bridge.

In the conjugates, bonded through amide bonds which conjugates include the immunogens of the present invention, the chemical bond between the carboxyl group containing gemcitabine haptens and the amino groups on the carrier or immunogen can be obtained using a variety of methods known to one skilled in the art. It is frequently preferable to form amide bonds by first activating the carboxylic acid moiety of the gemcitabine hapten in the compound of formula IV or their pharmaceutically acceptable salts by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the gemcitabine hapten of the compound of Formula IV or its pharmaceutically acceptable salts is then reacted in a buffered solution containing the protein carrier.

In preparing the amino bonded conjugates where the gemcitabine derivative of formula IV contains a primary or secondary amino group as well as the carboxyl group, it is necessary to use an amine protecting group during the activation and coupling reactions to prevent the conjugates from reacting with themselves. Typically, the amines on the gemcitabine derivative of formula IV are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. No. 3,996,344 and U.S. Pat. No. 4,016,146, which are herein incorporated by reference.

On the other hand in preparing amino conjugates where X is a terminal isocyanate or thioisocyanate radical in the compound of formula IV, these radicals when reacted with the free amine of a polyamine polymer produce the conjugate or immunogen of formula IV-B where X' is

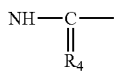

where $R_4$ is as above, which functionally connects with the amino group on the polyamine carrier or on the immunogenic polypeptide.

In preparing the amino conjugates of the compounds of formula IV where X is an aldehyde group these compounds may be connected to the amine group of the polyamine polypeptide or carrier through an amine linkage by reductive amination. Any conventional method of condensing an aldehyde with an amine such as through reductive amination can be used to form this linkage. In this case, X' in the ligand, portion of formula IV-B- is —$CH_2$.

The compound of formula IV and from this compound, the compound of formula IV-B, are prepared from gemcitabine (the compound of formula I). However in preparing the compound of formula IV, from the compound of formula I, it is necessary to selectively protect the hydroxy group of that 3' position and the amino group at the 4 position on the compound of formula I, what affecting the free hydroxy group at the 5' position to produce a compound of the formula.

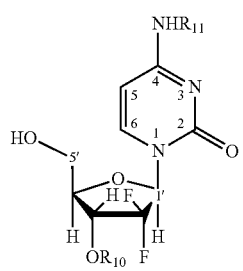

I-C wherein $R_{10}$ is a hydrolyzable hydroxy protecting group; and $R_{11}$ is a hydrolyzable amino protecting groups In preparing the compound of formula I-C the compound of formula I is reactive to convert the free hydroxy group to a hydrolyzable hydroxy protecting group. Any conventional method of converting a free hydroxy group into a hydrolyzable hydroxy protecting group can by used. This reaction should occur under mild alkaline conditions, so that the hydroxy group at the 3' position is protected while leaving the hydroxy group at the 5' position free. The hydroxy group at the 3' position in the compound of formula I-C is far more reactive than the hydroxy group at the 5' position. Therefore under mild alkaline aqueous conditions such as using sodium bicarbonate in an aqueous medium will provide a protecting group at the 3' hydroxy position without affecting the hydroxy group at the 5' position. Any conventional hydroxy protecting group which is easily hydrolizable can be utilitzed. The preferred hydroxy protecting group is a tertiary butoxy carbonyl group formed by reacting the compound of formula I with tertiary butoxy carbonate under mildly alkaline aqueous conditions at room temperature. Any other conventional hydroxy protecting groups can be utilized. Among the preferred hydroxy protecting groups are the ester groups formed by reacting the 3' hydroxy group in the compound of formula I with a alkanoic acid under mild alkaline conditions to form the ester at the 3' position while leaving the hydroxy group at the 5' position free. The compound of formula I with the protected 3' hydroxy group can be converted to the compound of formula I-C by the same reaction that was used to protect the hydroxy group at the 3' position except that elevated temperatures i.e. from 35° C. to 70° C. are utilized. In this manner the compound of formula I-C is formed from the compound of formula I.

The 5'-substituted compounds of formula IV where B is —$CH_2$— are formed by reacting the 5'-hydroxy group of gemcitabine with a halide of the formula:

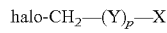 VIII-B wherein p, Y and X are as above.

In the next step of forming the compound of formula IV from gemcitabine, any conventional means of reacting an alcohol to form ethers can be utilized to condense the compound of formula VIII-B with the 5' hydroxy position on the gemcitabine. The use of a halide in the compound of formula VIII-B provides an efficient means for forming such ethers by condensing with the alcohol. On the other hand, where Y in the compound of formula VIII-B contains functional groups, which may interfere with this reaction to form the compound of formula II-B, these functional groups can be protected by means of suitable protecting groups which can be removed after this reaction as described hereinabove.

The 5'-substituted compounds of formula IV where B is

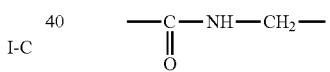

is produced by reacting 5'-hydroxy group on gemcitabine with an amino compound of the formula:

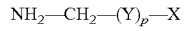 IX wherein X, Y and p are as above.

After first converting the 5'-hydroxy group on gemcitabine to the chloroformatic group

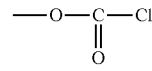

Any conventional means of converting a hydroxy group to a chloroformatic group can be used. After the formulation of a chloroformate, the halo group of the chloroformate is condensed with the amine group in the compound of formula IX. Prior to this reaction, the reactive group on gemcitabine and/or on the compound of formula IX are protected as described hereinabove with a conventional protecting group. These protecting groups can be removed after this halide condensation by conventional means such as described hereinbefore.

The compound of formula IV-B can be converted into the immunogens and/or the conjugate reagents of this invention by reacting these compounds with a polyamine or a polypeptide carrier which contains a terminal amino group. The same polypeptide can be utilized as the carrier and as the immunogenic polymer carrier in the immunogen of this invention provided that the polyamine or polypeptide carrier used to generate the antigen is immunologically active. However, to form the conjugates, these polymers need not produce an immunological response as needed for the immunogens. In accordance with this invention, the various functional groups represented by X in the compounds of formula IV-B can be conjugated to the polymeric material by conventional means of attaching a functional group to an amine or thiol group contained within the polymeric carrier.

The compounds of formula IV as either the reagent, conjugate including the immunogen prepared therefrom can be present or used in the immunoassay of this invention in its salt form or as a free base. The free amino group in the compound of formula IV and in the conjugate including immunogen prepared therefrom readily forms salts with acids preferably pharmaceutically acceptable acids. Any acid salt of the compound of formula IV and the conjugates including immunogen prepared therefrom can be used in this invention. These salts s including both inorganic and organic acids such as, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids.

Antibodies

The present invention also relates to novel antibodies including monoclonal antibodies to gemcitabine produced by utilizing the aforementioned immunogens. In accordance with this invention it has been found that these antibodies produced in accordance with this invention are selectively reactive with gemcitabine and do not react with non-pharmaceutically active metabolites and other compounds which would interfere with immunoassays for gemcitabine. The most problematic of these gemcitabine metabolites is 2',2'-difluoro-2'-deoxyuridine and the most problematic preservative is tetrahydrouridine. The ability of the antibodies of this invention not to react with these inactive metabolites and this preservative makes these antibodies particularly valuable in providing an immunoassay for gemcitabine.

The present invention relates to novel antibodies and monoclonal antibodies to gemcitabine. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and one or more subsequent booster shots of between 50 and 100 ug immunogen/mouse over a six month period. Through periodic bleeding, the blood samples of the immunized mice were observed to develop antibodies against gemcitabine utilizing conventional immunoassays. These methods provide a convenient way to screen for hosts which are producing antisera having the desired activity. The antibodies were also screened against the major pharmaceutically inactive metabolites of gemcitabine, particularly 2',2'-difluoro-2'-deoxyuridine and the preservative is tetrahydrouridine and showed no substantial binding to these compounds.

Monoclonal antibodies are produced conveniently by immunizing Balb/c mice according to the above schedule followed by injecting the mice with 100 ug immunogen i.p. or i.v. on three successive days starting four days prior to the cell fusion. Other protocols well known in the antibody art may of course be utilized as well. The complete immunization protocol detailed herein provided an optimum protocol for serum antibody response for the antibody to gemcitabine.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell. Murine hybridomas which produce gemcitabine monoclonal antibodies are formed by the fusion of mouse myeloma cells and spleen cells from mice immunized against gemcitabine-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988)).

The antibodies of this invention are selective for gemcitabine without having any substantial cross-reactivity with the major pharmaceutically non active metabolites of gemcitabine which is 2',2'-difluoro-2'-deoxyuridine and the preservative is tetrahydrouridine. By having no substantial cross-reactivity it is meant that the antibodies of this invention have a cross reactivity relative to gemcitabine with its non-pharmaceutically active metabolites, including the 2',2'-difluoro-2'-deoxyuridine and this preservative of less than 20%. Those antibodies having a cross reactivity of less than 15% are preferred.

Immunoassays

In accordance with this invention, the conjugates and the antibodies generated from the immunogens of the compounds of IV or salts thereof can be utilized as reagents for the determination of gemcitabine in patient samples. This determination is performed by means of an immunoassay. Any immunoassay in which the reagent conjugates formed from the compounds of IV or salts thereof compete with the gemcitabine in the sample for binding sites on the antibodies generated in accordance with this invention can be utilized to determine the presence of gemcitabine in a patient sample. The manner for conducting such an assay for gemcitabine in a sample suspected of containing gemcitabine, comprises combining an (a) aqueous medium sample, (b) an antibody to gemcitabine generated in accordance with this invention and (c) the conjugates formed from the compounds of formula IV or salts thereof. The amount of gemcitabine in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of gemcitabine.

Various means can be utilized to measure the amount of conjugate formed from the compounds of formula IV or salts thereof bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. Nos. 4,269,511 and 4,420,568.

On the other hand, the antibody can be coated or absorbed on nanoparticles so that when these particles react with the gemcitabine conjugates formed from the compounds formula IV or salts thereof, these nanoparticles form an aggregate. However, when the antibody coated or absorbed nanoparticles react with the gemcitabine in the sample, the gemcitabine from the sample bound to these nanoparticles does not cause aggregation of the antibody nanoparticles. The amount of aggregation or agglutination can be measured in the assay mixture by absorbance.

On the other hand, these assays can be carried out by having either the antibody or the gemcitabine conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula IV or salts thereof which is bound or unbound with the antibody. Other suitable labels include chromophores, fluorophores, etc.

As a matter of convenience, assay components of the present invention can be provided in a kit, a packaged combination with predetermined amounts of new reagents employed in assaying for gemcitabine. These reagents include the antibody of this invention, as well as, the conjugates formed from the compounds of formula IV or salts thereof. In addition to these necessary reagents, additives such as ancillary reagents may be included in these kits, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, the following abbreviations are used for designating the following:
EtOAc Ethyl acetate
$Na_2CO_3$ Sodium Bicarbonate
$Boc_2O$ Di-tert-butyl dicarbonate
CDI 1,1'-carbonyldiimidazole
$Na_2SO_4$ Sodium Sulfate
$CH_2Cl_2$ Dichloromethane
THF Tetrahydrofuran
$N_2$ Nitrogen gas
THF tetrahydrofuran
TFA trifluoroacetic acid
DMSO Dimethylsulfoxide
s-NHS sulfo-N-hydroxy succinimide
EDC 1-(3-dimethylaminopropyl)-3-ethylcarbodiimide hydrochloride
KLH Keyhole Limpet Hemocyanin
BSA Bovine serum albumin
PBS Phosphate buffered saline
NaCl sodium chloride
HRP horse radish-peroxidase
ANS 8-Anilino-1-naphthalenesulfonic acid
TMB 3,3',5,5'-Tetramethylbenzidine
TRIS Tris(hydroxymethyl)aminomethane hydrochloride
di-$H_2O$ deionized water The phosphate buffer composition has an aqueous solution containing
15.4 mM Sodium phosphate dibasic ($Na_2HPO_4$)
4.6 mM Sodium phosphate monobasic ($NaH_2PO_4$)
pH=7.2±0.10

In the Examples, Scheme 1 and Scheme 2 below set forth the specific compounds prepared and referred to by numbers in the Examples. The schemes are as follows:

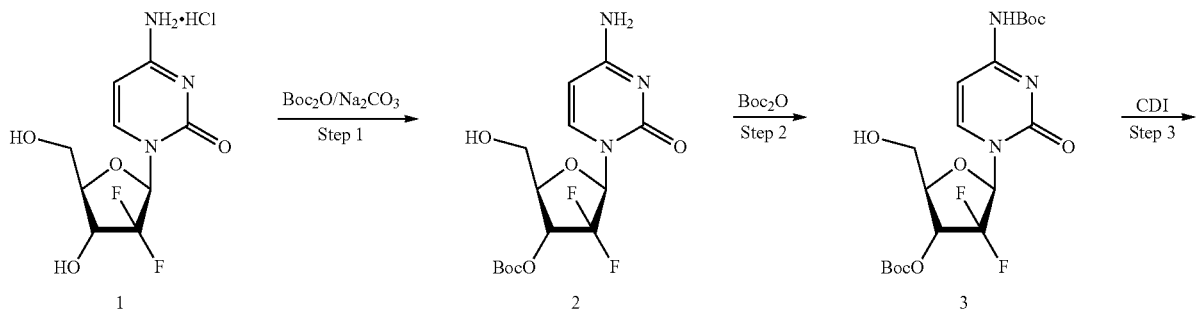

Scheme 1

-continued
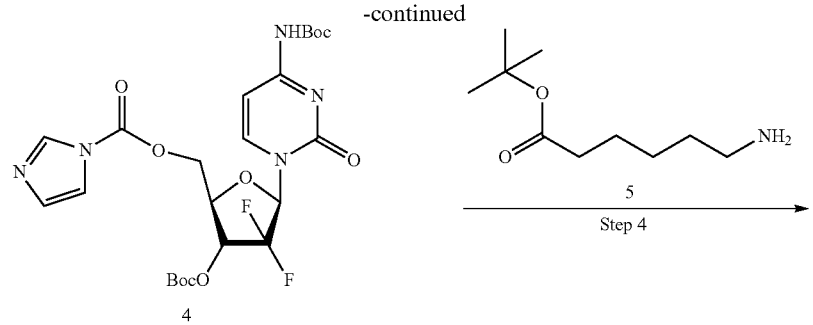
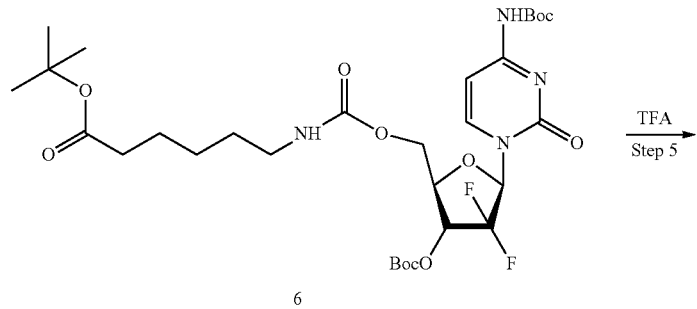
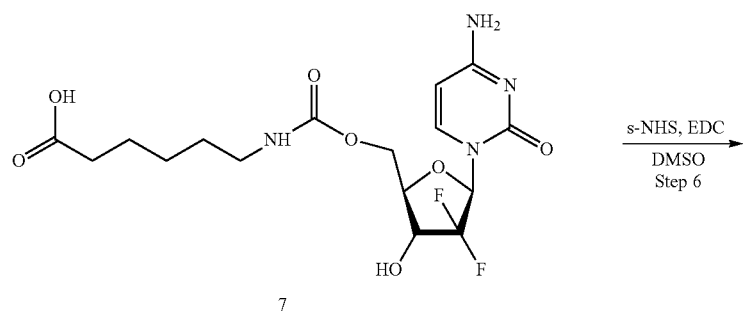
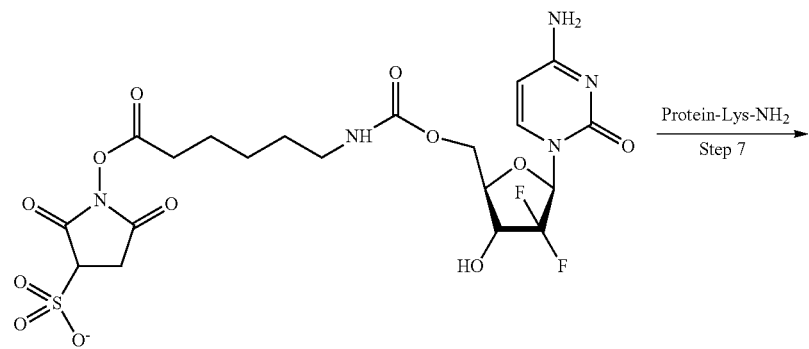
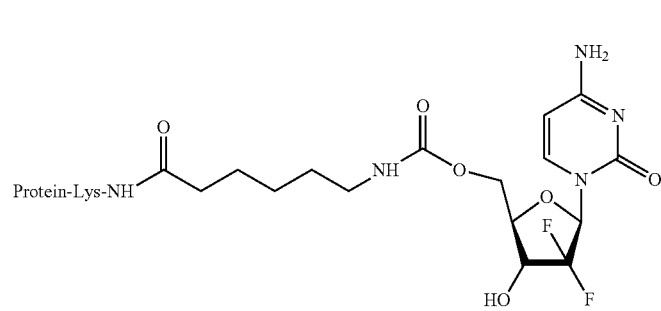

Scheme 2
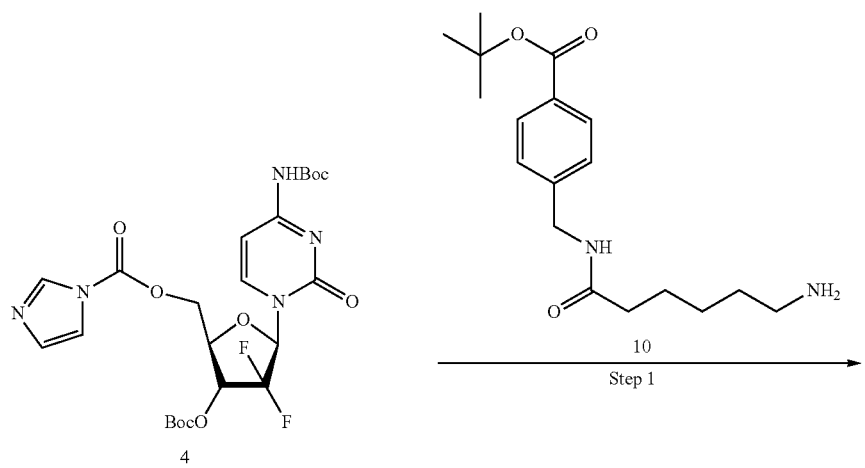
Step 1
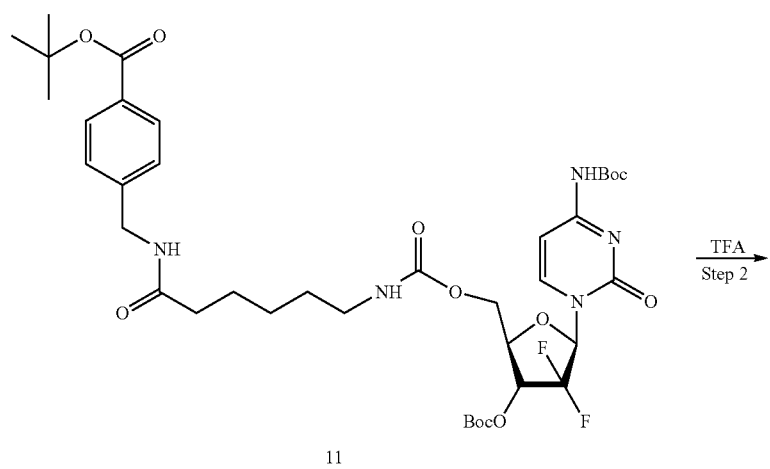
11    TFA, Step 2
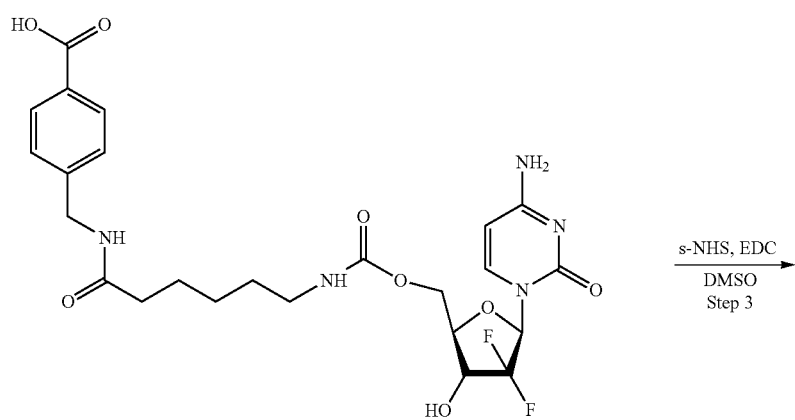
12    s-NHS, EDC, DMSO, Step 3

-continued

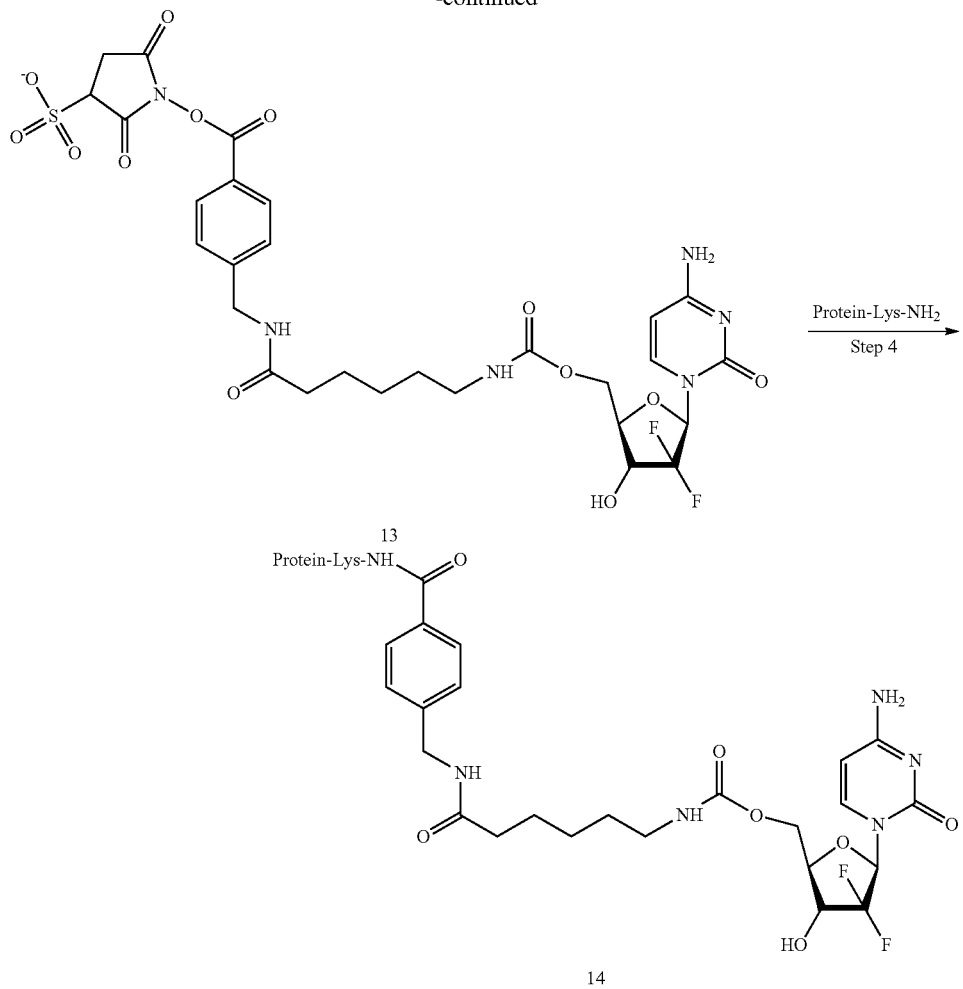

Example 1

Preparation of 5'-O—N-carbonyl(gemcitabine)-6'-aminocaproate [7] (scheme 1)

Compound [1] (1.2 g, 4.0 mmol) and Boc₂O (0.88 g, 4.0 mmol) were stirred in dioxane (60 mL) and a solution of Na₂CO₃ (2.12 g, 20.0 mmol) in water (15 mL) was added. The reaction mixture was stirred at 25° C. for 48 hours to produce [2] in the mixture. Water (40 mL) was added to the reaction mixture and the product [2] was extracted with EtOAc. The EtOAc organic phase was washed with brine, dried (Na₂SO₄), and evaporated to a white solid, which was then triturated with 10% CH₂Cl₂/hexanes to obtain compound [2] (1.26 g, 87%).

Compound [2] (1.25 g, 3.44 mmol) and Boc₂O (7.52 g, 34.40 mmol) were mixed in dioxane (100 mL) and heated at 37° C. for 48 hours to provide [3]. The solvent was evaporated to a white solid and the white solid was triturated with 10% CH₂Cl₂/hexanes to obtain the compound [3] (1.30 g, 82%).

Compound [3] (1.30 g, 2.80 mmol) and 1,1'-carbonyldiimidazole (0.52 g, 3.20 mmol) were mixed in THF (20 mL) and heated at 50° C. for 6 hours. The solvent was evaporated, the residue was dissolved in EtOAc, washed with water, dried with Na₂SO₄, and the solvent was evaporated to give compound [4] as a white solid (1.60 g, 100%).

Compound [4] (1.50 g, 2.69 mmol) and compound [5] (0.60 g, 3.23 mmol) were mixed in THF (20 mL) and heated at 50° C. for 24 hours. The reaction mixture was diluted with EtOAc, sequentially washed with water and brine, dried with Na₂SO₄, and evaporated to a white solid. This material was purified by flash chromatography with 10-50% EtOAc/hexanes to obtain compound [6] (1.40 g, 77%).

Compound [6] (1.40 g, 2.07 mmol) was dissolved in anhydrous CH₂Cl₂ (15 mL) and TFA (15 mL) was added to the stirred solution at 0° C. under N₂. The stirring was continued at 0° C. for 3 hours and then at 15° C. for 1 hour. The solvent was removed under reduced pressure, and the resulting residue was dissolved in water and lyophilized to isolate compound [7] (1.04 g, 94%) as a white powder.

Example 2

Preparation of 5'-O—N-carbonyl-(gemcitabine)-6'-methylcarbamoyl benzoic acid [12] (Scheme 2)

Compound [4] (0.60 g, 1.08 mmol) and compound [10] (0.38 g, 1.19 mmol) were mixed in THF (20 mL) and heated at reflux for 24 hours. The reaction mixture was diluted with EtOAc, washed sequentially with water and brine, dried with Na₂SO₄, and evaporated to a white solid. This material was purified by flash chromatography with 10-90% EtOAc/hexanes to obtain compound [11] (0.47 g, 54%).

Compound [11] (0.47 g, 0.58 mmol) was dissolved in anhydrous $CH_2Cl_2$ (10 mL) and TFA (10 mL) was added at 0° C. under $N_2$. The stirring was continued at 0° C. for 3 h and then at 15° C. for 1 h. The solvent was removed under reduced pressure and the resulting residue was dissolved in water and lyophilized to isolate compound [12] (0.33 g, 85%) as an off-white powder.

Example 3

General Method for Preparing s-NHS Activated Drug Derivatives from the Corresponding Acids [7] & [12]

Gemcitabine acid derivatives [7] & [12] were activated with EDC and s-NHS to produce the s-NHS activated esters of gemcitabine [8] & [13] for eventual conjugation to proteins (examples 4 and 5).

Example 3a

Preparation of s-NHS activated ester 5'-O—N-carbonyl(gemcitabine)-6'-aminocaproate Compound [7], example 1, scheme 1, (101.3 mg) was dissolved in 10 mL of DMSO to which was added s-NHS (121.7 mg) and EDC (107.1 mg). The reaction mixture was stirred for 20 hours at ambient temperature under a nitrogen atmosphere to produce compound [8]. The reaction mixture was used directly in examples 4 and 5a.

Example 3b

Preparation of s-NHS activated ester 5'-O—N-carbonyl-(gemcitabine)-6'-methylcarbamoyl benzoic acid [13]

Compound [12], example 2, scheme 2 (22.7 mg) was dissolved in 2.2 mL of DMSO and s-NHS (19.2 mg) and EDC (21.9 mg) were added. The reaction mixture was stirred for 20 hours at ambient temperature under a nitrogen atmosphere to produce compound [13]. The reaction mixture was used directly in example 5b.

Example 4

Preparation of KLH Immunogen with Activated Hapten, Gemcitabine-[9]-KLH

The s-NHS activated ester of gemcitabine [8] was conjugated with KLH to be used as the immunogen for monoclonal antibody development.

Example 4a

Preparation of the Gemcitabine-[9]-KLH Conjugate

A protein solution of KLH was prepared by dissolving 300 mg of KLH in 15 mL of phosphate buffer (50 mM, pH 7.5), followed by addition of 4.74 mL of compound [8] prepared in Example 3a. The reaction mixture of KLH and compound [8] was allowed to stir for 20 hours at room temperature to produce the gemcitabine [9]-KLH conjugate. The gemcitabine [9]-KLH conjugate was then purified by dialysis against 30% DMSO in phosphate buffer (50 mM, pH 7.5) at room temperature. Thereafter the DMSO proportion was reduced stepwise: 20%, 10% and 0%. The last dialysis was performed against phosphate buffer at 4° C. The gemcitabine [9]-KLH conjugate was characterized by ultraviolet-visible spectroscopy. The conjugate was diluted to a final concentration of 2 mg/mL in phosphate buffer (50 mM, pH 7.5).

Example 5a

Preparation of BSA Conjugate with Activated Hapten, Gemcitabine-[9]-BSA

A protein solution of BSA was prepared by dissolving 1 g BSA in phosphate buffer (50 mM, pH 7.5) for a final concentration of 50 mg/mL. To this protein solution was added 0.83 mL of s-NHS activated gemcitabine derivative [8] prepared in Example 3a. The amount of s-NHS activated gemcitabine derivative [8] added to the protein solution of BSA was calculated for a 1:1 molar ratio between the derivative of gemcitabine [8] and BSA. The mixture of BSA and activated gemcitabine derivative [8] was allowed to stir for 18 hours at room temperature to produce the conjugate of the activated gemcitabine ester [8] and BSA. This conjugate was then purified by dialysis against 20% DMSO in phosphate buffer (50 mM, pH 7.5) at room temperature. Thereafter the DMSO proportion was reduced stepwise: 10% and 0%. The last dialysis was performed against phosphate buffer at 4° C. The purified gemcitabine [9]-BSA conjugate was characterized by UV/VIS spectroscopy.

Example 5b

Preparation of BSA Conjugate with Activated Hapten [13] Gemcitabine-[14]-BSA

A protein solution of BSA was prepared by dissolving 1 g BSA in phosphate buffer (50 mM, pH 7.5) for a final concentration of 50 mg/mL. To 10.0 mL of the protein solution of BSA while stirring on ice, was added 0.620 mL of s-NHS activated gemcitabine derivative [13] prepared in Example 3b. The amount of s-NHS activated gemcitabine derivative [13] added to the protein solution of BSA was calculated for a 1:1 molar ratio between the derivative of gemcitabine [15] and BSA. The mixture of BSA and activated gemcitabine derivative [15] was allowed to stir for 18 hours at room temperature to produce the conjugate of the activated gemcitabine ester [15] and BSA. This conjugate was then purified by dialysis against 15% DMSO in phosphate buffer (50 mM, pH 7.5) at room temperature. Thereafter the DMSO proportion was reduced stepwise: 10%, 5%, and 0%. The last dialysis was performed against phosphate buffer at 4° C. The purified gemcitabine [14]-BSA conjugate was characterized by UV/VIS spectroscopy.

Example 6

Preparation of Polyclonal Antibodies to Gemcitabine [9]

Ten female BALB/c mice were immunized i.p. with 100 μg/mouse of gemcitabine [9]-KLH immunogen, as prepared in Example 4, emulsified in Complete Freund's adjuvant. The mice were boosted once, four weeks after the initial injection with 100 μg/mouse of the same immunogen emulsified in Incomplete Freund's Adjuvant. Twenty days after the boost, test bleeds containing polyclonal antibodies from each mouse were obtained by orbital bleed. The anti-serum from these test bleeds containing gemcitabine antibodies were evaluated in Examples 8 and 9.

Example 7a

Microtiter Plate Sensitization Procedure with Gemcitabine [9]-BSA Conjugate The ELISA method for measuring Gemcitabine concentrations was performed in polystyrene microtiter plates (Nunc MaxiSorp F8 Immunomodules) optimized for protein binding and containing 96 wells per plate. Each well was coated with Gemcitabine [9]-BSA conjugate (prepared as in Example 5a) by adding 300 µL of Gemcitabine [9]-BSA conjugate at 10 µg/mL in 0.05M sodium carbonate, pH 9.6, and incubating for three hours at room temperature. The wells were washed with 0.05 M sodium carbonate, pH 9.6 and then were blocked with 375 µL of 5% sucrose, 0.2% sodium caseinate solution for 30 minutes at room temperature. After removal of the post-coat solution the plates were dried at 37° C. overnight.

Example 7b

Microtiter Plate Sensitization Procedure with Gemcitabine [14]-BSA Conjugate The ELISA method for measuring Gemcitabine concentrations was performed in polystyrene microtiter plates (Nunc MaxiSorp F8 Immunomodules) optimized for protein binding and containing 96 wells per plate. Each well was coated with Gemcitabine [14]-BSA conjugate (prepared as in Example 5b) by adding 300 µL of gemcitabine [14]-BSA conjugate at 10 µg/mL in 0.05M sodium carbonate, pH 9.6, and incubating for three hours at room temperature. The wells were washed with 0.05M sodium carbonate, pH 9.6 and then were blocked with 375 µL of 5% sucrose, 0.2% sodium caseinate solution for 30 minutes at room temperature. After removal of the post-coat solution the plates were dried at 37° C. overnight.

Example 8

Antibody Screening Procedure—Titer

This procedure is to find the dilution of antibody to be tested for displacement as in Example 9. The ELISA method for screening gemcitabine antibodies (produced in Example 6) was performed with the microtiter plates that were sensitized with gemcitabine-BSA conjugate prepared in Examples 7a and 7b. The antibody screening assay was performed by diluting the murine serum from test bleeds (as in Example 6) containing polyclonal gemcitabine antibodies to 1:10, 1:100, 1:1,000 and 1:10,000 (volume/volume) in phosphate buffered saline containing 0.1% BSA and 0.01% thimerosal. To each well of gem citabine-BSA sensitized wells (prepared in Examples 7a and 7b) 50 µL phosphate buffered saline containing 0.1% BSA and 0.01% thimerosal and 50 µL of diluted antibody were added and incubated for 10 minutes at room temperature with shaking. During this incubation antibody binds to the gemcitabine-BSA conjugate passively absorbed in the wells (Examples 7a and 7b). The wells of the plates were washed three times with 0.02 M TRIS, 0.9% NaCl, 0.5% Tween-80 and 0.001% thimerosal, pH 7.8 to remove any unbound antibody. To detect the amount of Gemcitabine antibody bound to the gemcitabine-BSA conjugate in the wells, 100 µL of a goat anti-mouse antibody-HRP enzyme conjugate (Jackson Immunoresearch) diluted to a specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody-HRP enzyme conjugate binds to gemcitabine antibodies in the wells, the plates were again washed three times to remove unbound goat anti-mouse antibody-HRP enzyme conjugate. To develop a measurable color in the wells washing was followed by the addition of 100 µL of TMB (TMB Substrate, BioFx), the substrate for HRP, to develop color form minutes shaking at room temperature. Following the incubation for color development, the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing antibody dilution of the antibody measured (x-axis) vs. absorbance 650 nm (y-axis) and interpolating the titer at an absorbance of 1.5. The titer which produced absorbance of 1.5 determined the concentration (dilution) of antibody used in the indirect competitive microtiter plate assay described in Example 9.

Example 9

Indirect Competitive Microtiter Plate Immunoassay Procedure Determining $IC_{50}$ and Cross-Reactivity for Antibodies to Gemcitabine The ELISA method for determining $IC_{50}$ values and cross-reactivity was performed with the microtiter plates that were sensitized with gemcitabine-BSA conjugates as described in Examples 7a and 7b. The analytes—gemcitabine and 2',2'-difluoro-2'-deoxyuridine were diluted in $diH_2O$ over a concentration range of 1 to 10,000 ng/mL for gemcitabine [9]-BSA microtiter plates and 0.5 to 1,000 ng/mL for gemcitabine [14]-BSA microtiter plates. Each of the assays were performed by incubating 50 µL of the analyte solution with 50 µL of one of the antibodies selected from the polyclonal antibodies produced in Example 6 with the immunogen of Example 4. The assays were all performed by diluting the concentration of the antibodies in each of the wells to the titer determined in Example 8. During the 10 minute incubation (at room temperature with shaking) there is a competition of antibody binding for the gemcitabine-BSA conjugate in the well (produced in Examples 7a and 7b) and the analyte in solution. Following this incubation the wells of the plate were washed three times with 0.02 M TRIS, 0.9% NaCl, 0.5% Tween-80 and 0.001% thimerosal, pH 7.8 to remove any material that was not bound. To detect the amount of gemcitabine antibody bound to the gemcitabine-BSA conjugate in the wells (produced in Examples 7a and 7b), 100 µL of a goat anti-mouse antibody-HRP enzyme conjugate (Jackson Immunoresearch) diluted to a predetermined specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody-HRP enzyme conjugate binds to gemcitabine antibodies in the wells, the plates were again washed three times to remove unbound secondary conjugate. To develop a measurable color in the wells washing was followed by the addition of 100 µL of TMB (TMB Substrate, BioFx), the substrate for HRP, to develop color in a 10 minute incubation with shaking at room temperature. Following the incubation for color development, 50 µL of stop solution (1.5% sodium fluoride in $di-H_2O$) was added to each well to stop the color development and after 20 seconds of shaking the absorbance was determined at 650 nm (Molecular Devices Plate Reader). The amount of antibody in a well was proportional to the absorbance measured and inversely proportional to the amount of gemcitabine in the sample. The $IC_{50}$ values of gemcitabine and 2',2'-difluoro-2'-deoxyuridine were determined by constructing dose-response curves with the absorbance in the wells plotted versus analyte concentration in the wells. The absorbance of the color in the wells containing analyte was compared to that with no analyte and a standard curve was generated. The $IC_{50}$ value for a given analyte was defined as the concentration of analyte that was required to have 50% of the absorbance of the wells containing no analyte. The cross-reactivity was calculated as the ratio of the $IC_{50}$ for gemcitabine to the $IC_{50}$ value for 2',2'-difluoro-2'-deoxyuridine and expressed as a percent. When measured with this pool of antibodies, the percent cross-reactivities relative to gemcitabine for 2',2'-difluoro-2'-deoxyuridine were 0.2-0.8%, and the percent cross-reactivities relative to gemcitabine for 3,4,5,6-tetrahydrouridine were 0.009-0.1%. Results for monoclonal antibodies to gemcitabine are in table I below.

TABLE I

Cross-reactivity of competitive immunoassay using monoclonal antibodies to gemcitabine (Example 9).

| | Plates coated with gemcitabine[9]-BSA conjugate (Example 9) | | | | |
|---|---|---|---|---|---|
| Subclone # | Gemcitabine IC50 (ng/mL) | dFdU IC50 (ng/mL) | THU IC50 (ng/mL) | % cross-reactivity dFdU | % cross-reactivity THU |
| 5H8-24 | 11 | 3530 | >100,000 | 0.2 | <0.009 |
| 2F12-24 | 31 | 8294 | >100,000 | 0.4 | <0.03 |
| 12A5-24 | 14 | 4748 | >100,000 | 0.3 | <0.01 |
| 14G3-15 | 9 | 3709 | >100,000 | 0.3 | <0.1 |
| 3E10-6 | 136 | 16341 | >100,000 | 0.8 | <0.009 |

As seen from these tables, the antibodies of this invention are substantially selectively reactive with the active form of gemcitabine with minimal cross-reactivity with both the inactive metabolite 2',2'-difluoro-2'-deoxyuridine and 3,4,5,6-tetrahydrouridine.

The invention claimed is:

1. An immunoassay for detecting gemcitabine in a sample comprising providing a mixture of a) said sample, b) an antibody selectively reactive with gemcitabine and not substantially cross-reactive with 2',2'-difluoro-2'-deoxyuridine and tetrahydrouridine, and c) a conjugate of a carrier having either a reactive thiol or amino group with a compound of the formula:

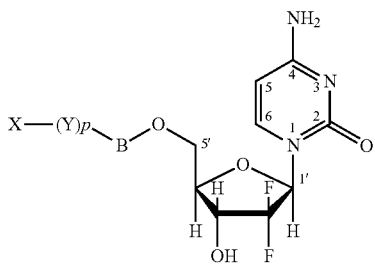

IV wherein B is

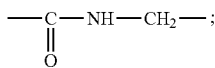

Y is an organic spacing group;
X is a functional group capable of binding to said carrier through said amino or thiol group; and
p is an integer from 0 to 1
or salts thereof;
causing the gemcitibine in the sample and said conjugate in said mixture to bind with said antibody and thereafter measuring the amount of said conjugate in said mixture which is bound or unbound to said antibody whereby the presence of gemcitibine in the sample can be determined.

2. The process of claim 1, wherein the sample is a human sample.

3. The immunoassay of claim 2, wherein said antibody is generated from an immunogen comprising an immunogenic carrier having a reactive thiol or amino group conjugated to a compound of the formula:

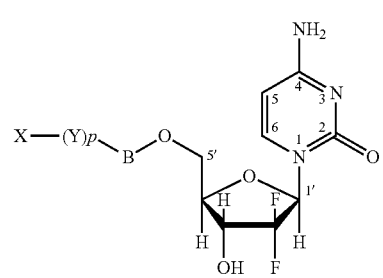

IV wherein p, X, Y and B are as above;
or salts thereof.
wherein p, X, Y and A are as above.

4. The immunoassay of claim 3, wherein the carrier contains a thiol group and X is the compound which is linked to the immunogenic polymer is a functional group capable of reacting with said thiol.

5. The immunoassay of claim 4, wherein X is

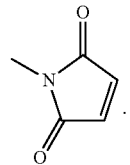

6. The immunoassay of claim 5, wherein Y is lower alkylene.

7. The immunoassay of claim 6 wherein the immunogenic carrier contains as the functional group

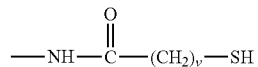

wherein v is an integer from 1 to 6.

8. The immunoassay of claim 2, wherein the antibody is attached to a solid support.

9. The immunoassay of claim 8, wherein the solid support is microtiter plates.

10. The immunoassay of claim 9, wherein the solid support is nanoparticles.

* * * * *